United States Patent [19]

Mak

[11] Patent Number: 5,530,178
[45] Date of Patent: Jun. 25, 1996

[54] MUTANT MOUSE LACKING CD8 SURFACE MARKER

[75] Inventor: Tak W. Mak, Toronto, Canada

[73] Assignee: The Ontario Cancer Institute, Toronto, Canada

[21] Appl. No.: 97,930

[22] Filed: Jul. 28, 1993

Related U.S. Application Data

[63] Continuation-in-part of Ser. No. 707,036, May 29, 1991, abandoned.

[51] Int. Cl.$^6$ ............................. C12N 5/00; C12N 15/00
[52] U.S. Cl. .................... 800/2; 800/DIG. 1; 435/172.3; 435/240.2; 435/320.1; 935/111
[58] Field of Search ................................ 800/2, DIG. 1, 800/DIG. 2, DIG. 3; 435/240.2, 172.3, 317.1, 320.1; 935/70, 111

[56] References Cited

PUBLICATIONS

Fung–Leung et al., Cell 65:443–449 (1991).
Koller et al. (a), Science 248:1227–1230 (1990).
Koller et al. (b), Proc. Natl. Acad. Sci. 86:8932–8935 (1989).
Zijlstra et al., Nature 342:435–438 (1989).
Killeen et al., J. Cell Biochem. Suppl. 0(14 Part A):361 (1990).
Doetschman et al., Proc. Natl. Acad. Sci. 85:8583–8587 (1988).
Joyner et al., Nature 338:153–156 (1989).
Liaw et al., J. Immunol. 137:1037–1043 (1986).
Nakauchi et al., Proc. Natl. Acad. Sci. 82:5126–5130 (1985).

*Primary Examiner*—Jasemine C. Chambers
*Attorney, Agent, or Firm*—Marshall, O'Toole, Gerstein, Murray & Borun

[57] ABSTRACT

A mutant mouse strain without CD8 (Lyt-2 and Lyt-3) expression on the cell surface has been generated by disrupting the Lyt-2 gene using embryonic stem cell technology. In these mammals, for example, mice, $CD8^+$ T lymphocytes are not present in peripherial lymphoid organs, but the $CD4^+$ T lymphocyte population seems to be unaltered. Cytotoxic response of T lymphocytes from these mice against alloantigens and viral antigens is dramatically decreased. Proliferative response against alloantigens and in vivo help to B lymphocytes, however, are not effected. These mice should be useful for drug development and for studies of diseases of the immune system such as, autoimmunity, immunodeficiency, transplant rejection and tumor rejection.

4 Claims, 9 Drawing Sheets

5,530,178

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AACGCACGGG TGTTGGGTCG TTTG        24

( 2 ) INFORMATION FOR SEQ ID NO:2:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

ATTCAAGGCC AACCTTTGCC 20

MUTANT MOUSE LACKING CD8 SURFACE MARKER

This application is a continuation-in-part of application Ser. No. 07/707,036, filed May 29, 1991, now abandoned.

The invention is a mutant mouse lacking the CD8 surface marker on its T lymphocytes. The invention as expressed, for example, in mutant mice is useful for the study of CD8 in T cell maturation and the function of CD8$^+$ T cells in the immune system. The invention is useful in the development of clinical or diagnostic applications relating to auto-immune diseases, viral infections, parasite infections and other such medical conditions as will be apparent to the skilled person.

T cells recognize processed antigenic peptides in association with class I or class II molecules encoded by the major histocompatibility complex (MHC). The antigen specificity of T cells is mainly attributed to the T cell receptor (TcR). Class I and class II MHC restricted T cells can be distinguished from each other by the presence of the surface markers CD8 and CD4, respectively. CD8$^+$ T cells are usually cytotoxic cells (CTL) responding to antigenic challenge by lysis of the target cells, while CD4$^+$ T cells are helper cells which produce lymphokines and play a role in the activation or proliferation or both of B cells, CTL, and macrophages.

Maturation of T cells in the thymus involves the processes of selection for tolerance of self-antigens (negative selection) and acquisition of restriction to self-MHC molecules (positive selection). T cell precursors entering the thymus initially do not express CD4, CD8 or CD3 on their surface. They differentiate in the thymus through a series of intermediates, including a transient stage of CD8$^+$ cells which lack T cell receptor, to a stage when CD4, CD8, and low levels of TcR are expressed on the cell surface. It is at this stage of development that the T cells undergo positive and negative selection and eventually emerge from the thymus as mature CD8$^+$CD4$^-$ or CD4$^+$CD8$^-$ (single positive) T cells.

The present invention provides a mutant mouse lacking the CD8 surface marker on its T cells. Particularly described are genetically manipulated mice that lack cell surface expression of CD8. The invention was obtained in mice by disruption of the coding sequence of the murine Lyt-2 gene by homologous recombination (Smithies et al., 1985) in embryonic stem (ES) cells (Thomas and Capecchi, 1987). The ES cells have the potential to contribute to all tissues including the germ-line when they are introduced into mouse preimplantation embryos (Gossler et al., 1986; Robertson et al., 1986). Subsequent breeding of the mice allows the generation of a new mouse strain, homozygous for the genetic change.

Generation of Mice Without CD8 Surface Expression

Figure 1:
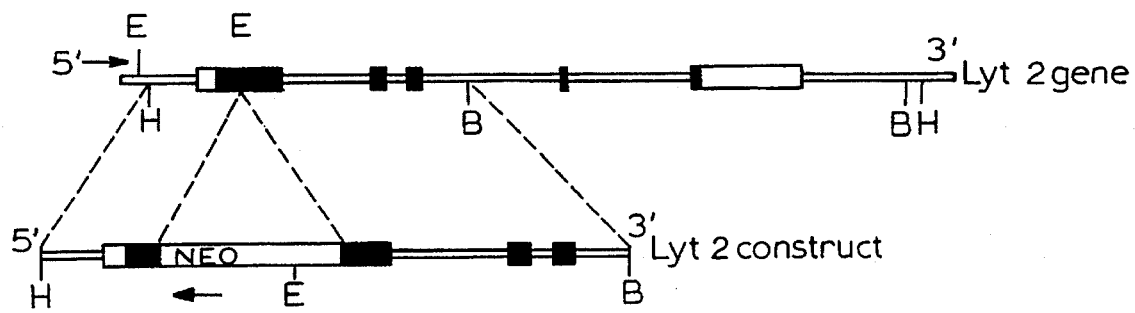
FIG. 1 shows schematic diagrams of the mouse Lyt-2 gene and the Lyt-2 construct for homologous recombination. The boxes indicate exons of the Lyt-2 gene with black shading to denote coding regions. The neomycin resistant gene (neo) was inserted as described in Experimental Procedures. Arrows indicate the positions and directions (5' to 3') of the primers used in PCR screening as described in Experimental Procedures. Restriction enzyme sites are B, BamHI; E, EcoRI; H, HindIII.

CD8 in the mouse is encoded by two genes, Lyt-2 and Lyt-3 (Zamoyska et al., 1985; Nakauchi et al., 1987) and is expressed on the T cell surface predominantly as a disulfide-linked heterodimer of Lyt-2 and Lyt-3 (Ledbetter et al., 1981; Walker et al., 1984a; b). Lyt-2 can also be expressed on the cell surface as a homodimer in transfected cells (Zamoyska et al., 1985; Gorman et al., 1988), but the surface expression of Lyt-3, at least in T cell lines, appears to require the presence of the Lyt-2 molecule (Blanc et al., 1988; Gorman et al., 1988; Schmidt-Ullrich and Eichmann, 1990). Therefore, the Lyt-2 gene was disrupted to generate a mutant mouse strain without cell surface expression of CD8. The Lyt-2 gene contains five exons spanning a region of 4.4 kb (Liaw et al., 1986). To disrupt the Lyt-2 gene by homologous recombination, a 2.2 kb HindIII-BamHI DNA fragment containing exons 1, 2, and 3 of the Lyt-2 gene was used as a construct and the coding sequence was interrupted by inserting the neomycin resistance gene (Thomas and Capecchi, 1987) into the EcoRI site of exon 1 (FIG. 1). This DNA construct was introduced into D3 embryonic stem cells (Doetschman et al., 1985) by electroporation. G418-resistant colonies were screened for the homologous recombination event between the construct and the endogenous Lyt-2 gene by the polymerase chain reaction (PCR). The average frequency of homologous recombination was about 1 in 10$^7$ electroporated cells or 1 in 200 G418-resistant clones.

ES cell lines with the disrupted Lyt-2 gene were injected into 3.5 day old C57BL/6 blastocysts and chimeric mice were obtained. Male chimeric mice were tested for germ-line transmission of the mutation and chimeric mice from one of the cell lines were shown to generate offspring heterozygous for the mutation. Mice carrying the disrupted Lyt-2 gene were identified by tail DNA analysis and were interbred to obtain mice homozygous for the mutant gene.

Phenotypic Analysis of Mutant Mice

Mice heterozygous and homozygous for the disrupted Lyt-2 gene appeared to be healthy and were fertile. Gross inspection of the lymphoid organs of the homozygous mice (i.e. thymus, lymph node, spleen) did not show any sign of atrophy. The anatomical distribution of lymphoid and stromal cells in the thymus of the mutant mice was shown to be normal by immunohistochemical methods using monoclonal antibodies against CD3, CD4 and Lyt-2 on thymocytes, and antibodies ER-TR4 and ER-TR5 which recognize cortical and medullary epithelial cells, respectively (data not shown). Numbers of cells in lymphoid organs were similar to those of normal mice. The ratio of T and B cells in lymph nodes of these mice was normal as identified by antibodies specified for Thy-1.2 and immunoglobulin M, respectively, in flow cytometric analysis (data not shown). Both the heterozygous and homozygous mice expressed normal levels of MHC class I and class II proteins as determined by florescence cell activating staining (data not shown). "Normal" here refers to that expression level found in wild-type mice.

Figure 2A:
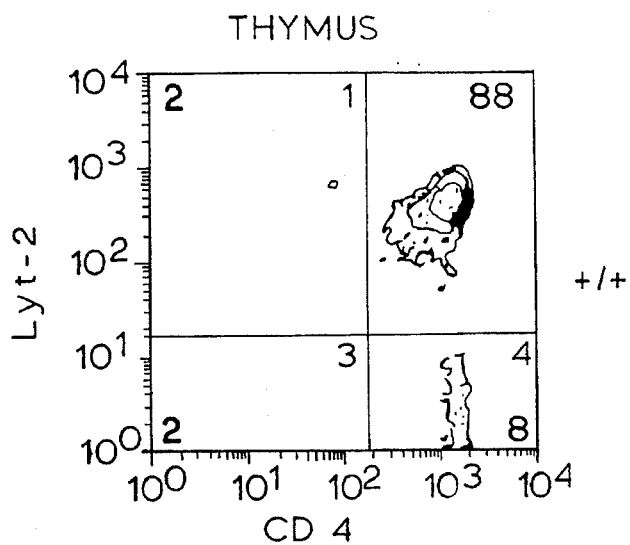
FIGS. 2A, 2B, 2C, 2G, 2H, 2I, 2M, 2N, and 2O show flow cytometric analyses of thymus cells from wild-type mice (+/+) and mice heterozygous (+/−) and homozygous (−/−) for the disrupted Lyt-2 gene.
Figure 2B:
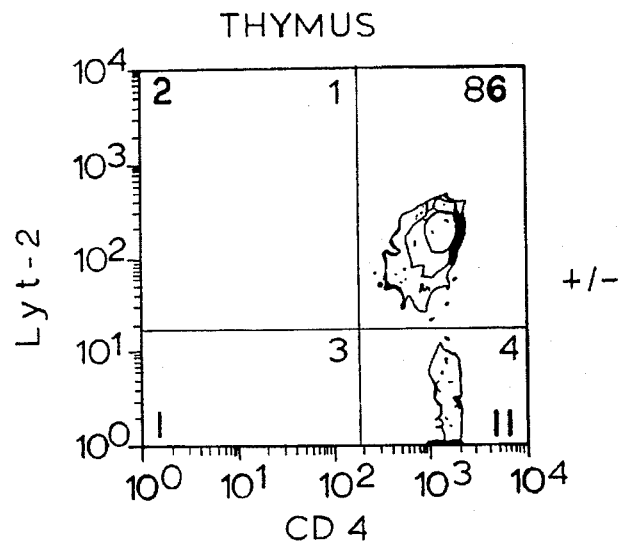

Surface expression of Lyt-2 was not detected on thymocytes and lymph node cells from mice homozygous for the disrupted Lyt-2 gene (FIG. 2A). Interestingly, the intensity of the staining for Lyt-2 in heterozygous mice was about half of that of wild-type mice. These data suggest that the Lyt-2 genes of both maternal and paternal origin contribute to the level of Lyt-2 expression. Similar results were found when these cells were stained with a monoclonal antibody against Lyt-3 (FIG. 2B), suggesting that surface expression of Lyt-3 is dependent on concomitant Lyt-2 expression in most, if not all, thymocytes and T lymphocytes. The reduction in the level of Lyt-3 surface expression in heterozygous mice suggests that Lyt-2 is the limiting molecule for surface expression of CD8.

Absence of Class I MHC Restricted Cytotoxic T Cells

Figure 2C:
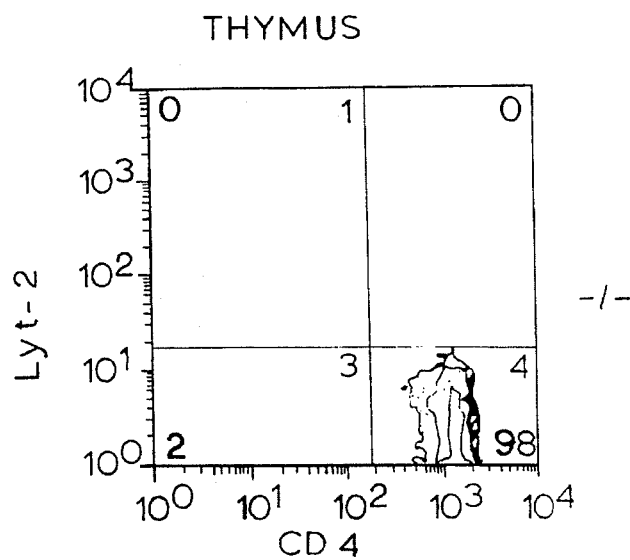
Figure 2D:
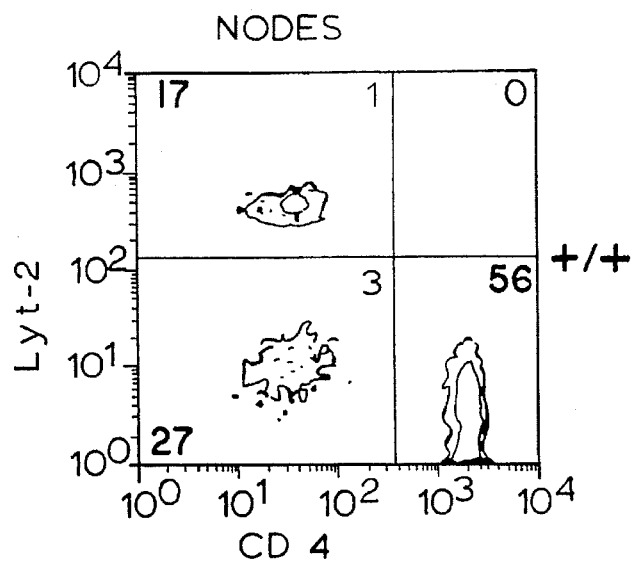
FIGS. 2D, 2E, 2F, 2J, 2K, 2L, 2P, 2Q, and 2R show flow cytometric analyses of lymph node cells from wild-type mice (+/+) and mice heterozygous (+/−) and homozygous (−/−) for the disrupted Lyt-2 gene. Samples were stained for Lyt-2 and CD4 (FIGS. 2A, 2B, 2C, 2D, 2E, and 2F), Lyt-3 and CD4 (FIGS. 2G, 2H, 2I, 2J, 2K, and 2L), or CD3 and CD4 (FIGS. 2M, 2N, 2O, 2P, 2Q, and 2R).
Figure 2E:
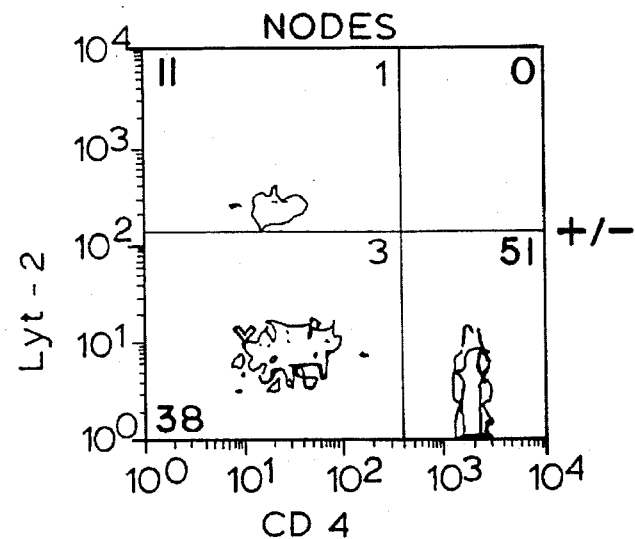
Figure 2F:
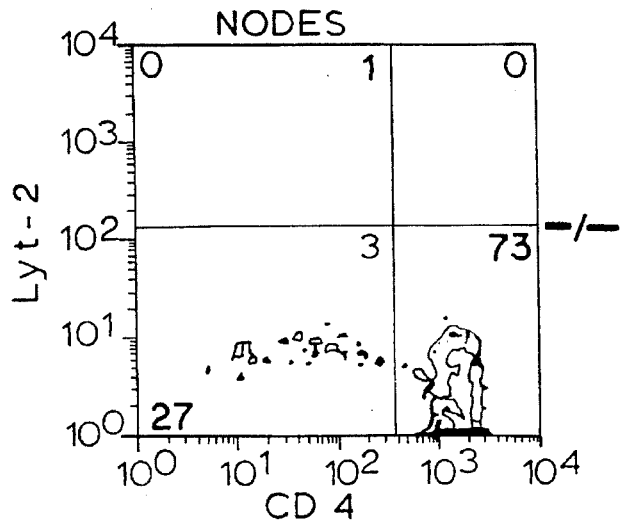
Figure 2G:
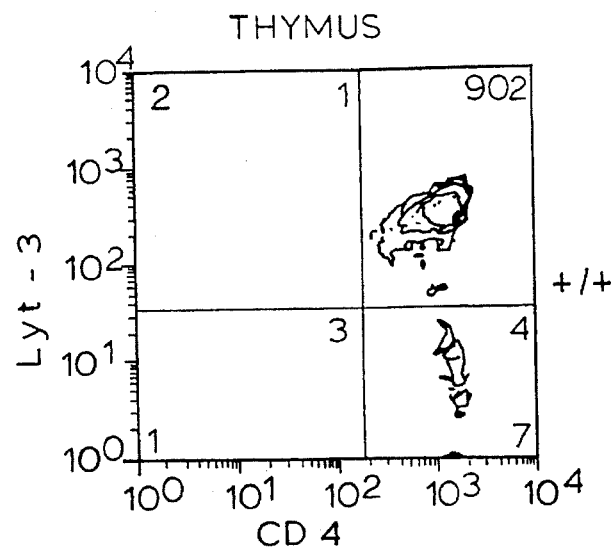
Figure 2H:
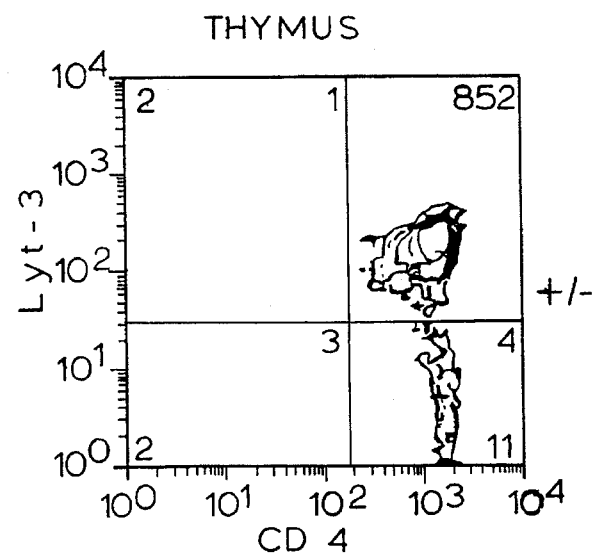
Figure 2I:
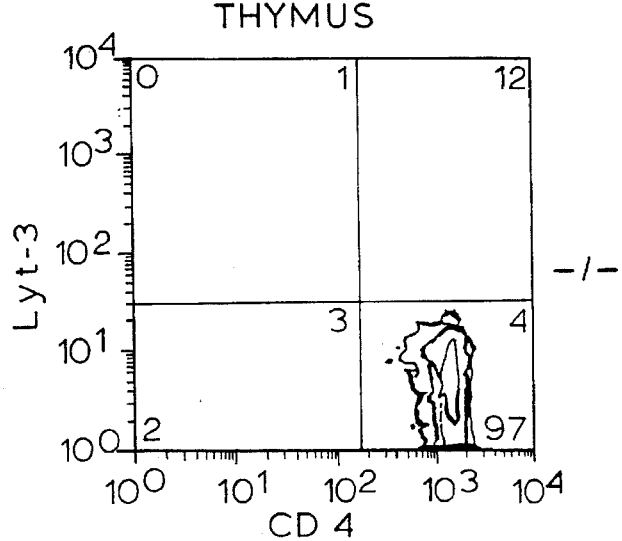
Figure 2J:
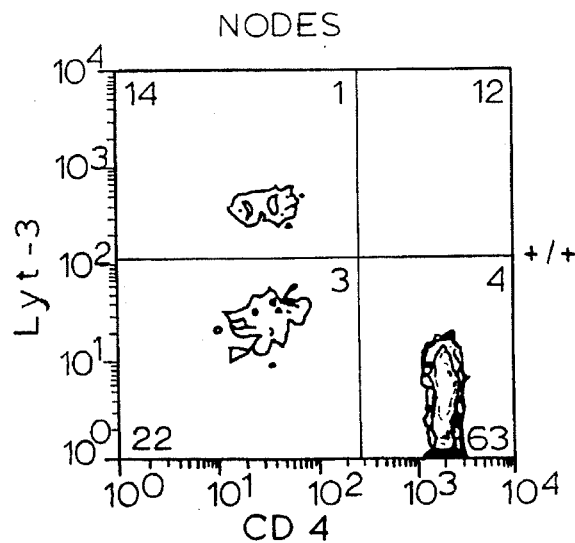
Figure 2K:
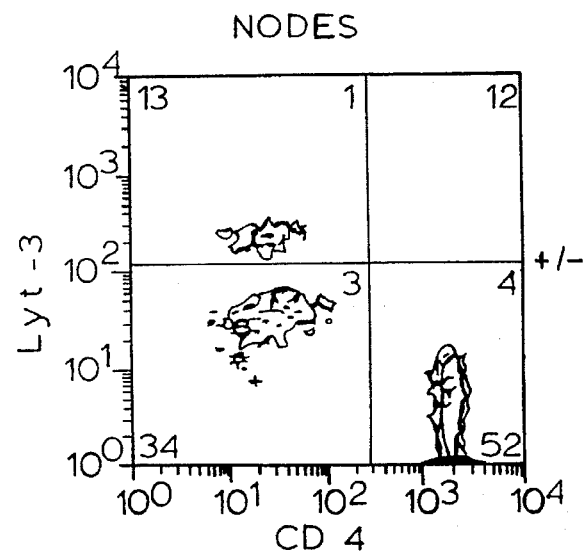
Figure 2L:
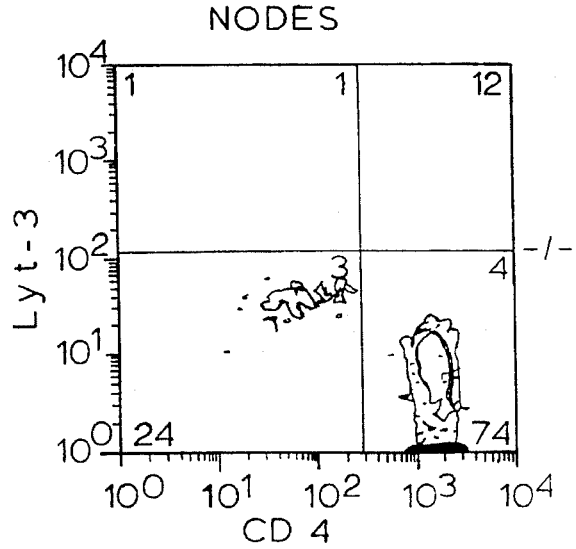
Figure 2M:
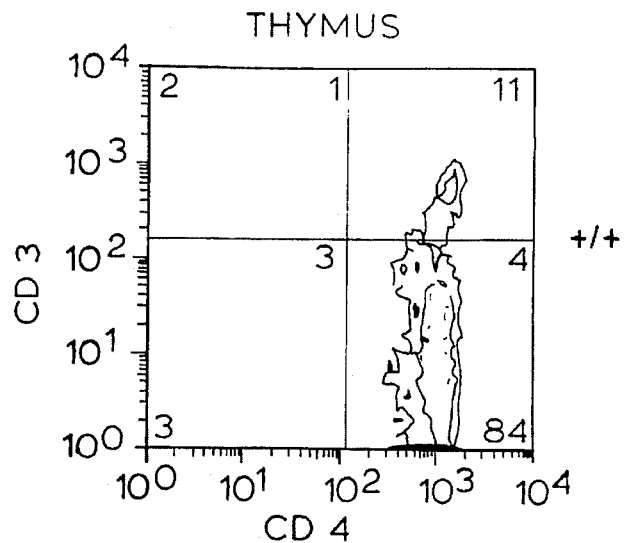
Figure 2N:
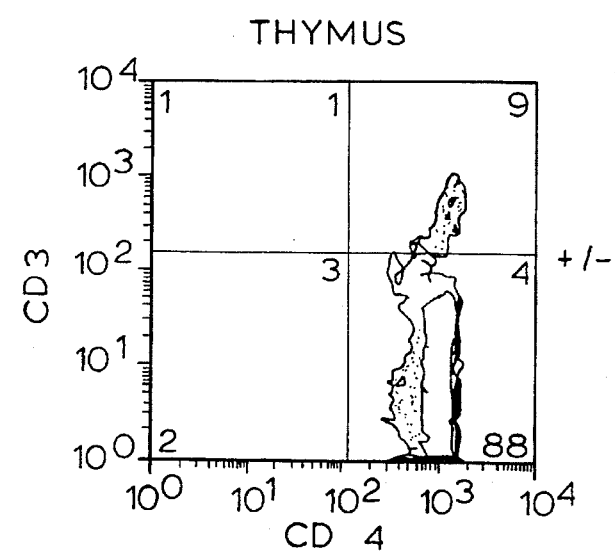
Figure 2O:
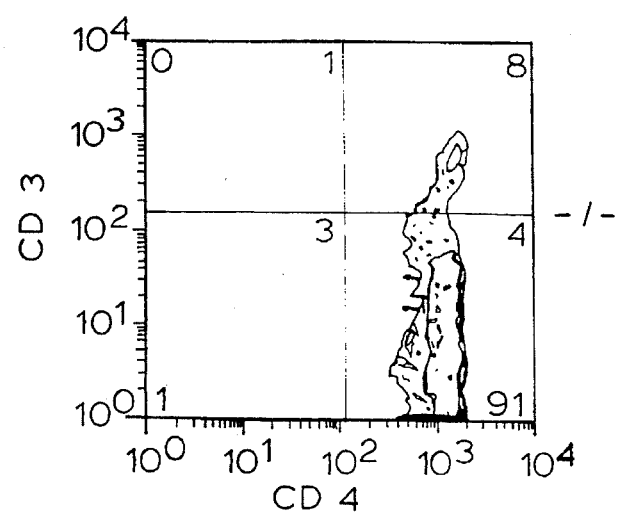
Figure 2P:
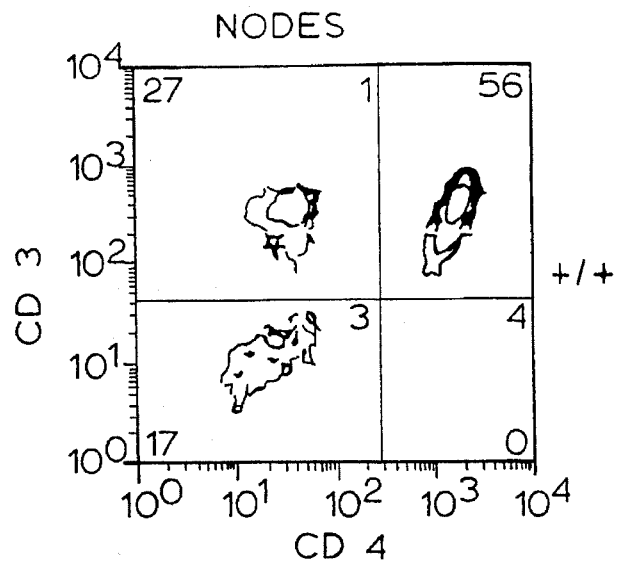
Figure 2Q:
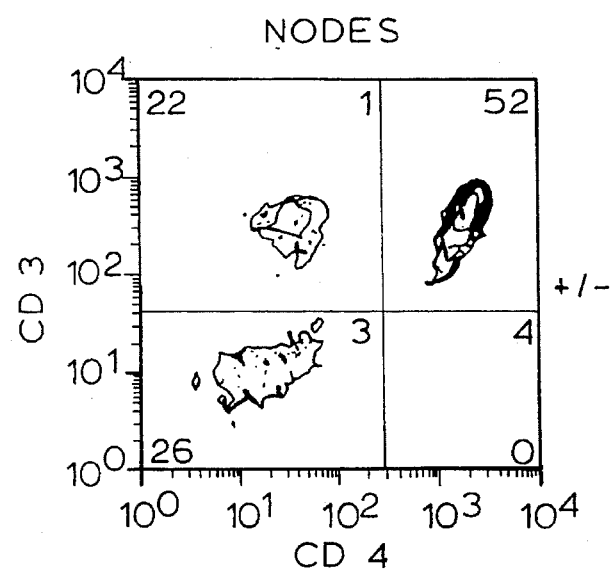
Figure 2R:
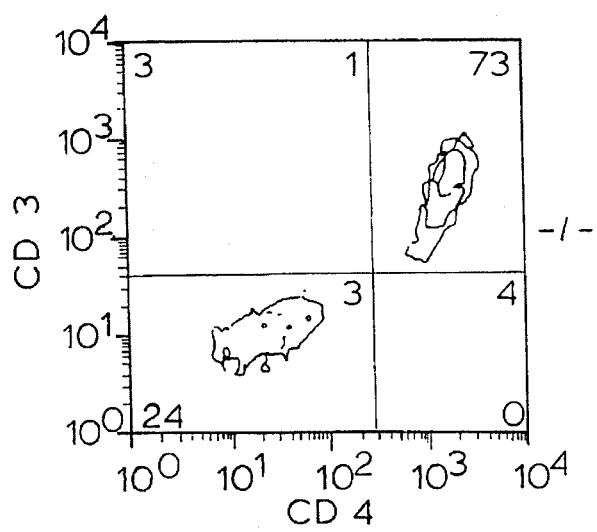

Murine cytotoxic T cells are usually of the $CD8^+CD4^-$ phenotype. This population was absent from the thymus and lymph nodes of mice homozygous for the disrupted Lyt-2 gene (FIG. 2A and B). It is possible that mature T cells, normally bearing CD8, might still be present in the homozygous mouse but would now simply be lacking CD8 expression on the cell surface. The thymocytes and lymph node cells were therefore stained with antibodies against CD4 and CD3 to examine this possibility (FIG. 2C). There is no indication of a significant $CD3^+CD4^-$ population.

Figure 3A:
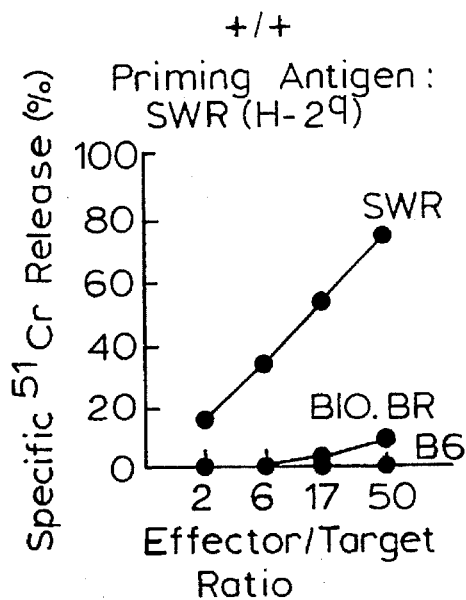
FIG. 3 shows cytotoxic activities of T cells from spleens of wild-type mice (+/+), heterozygous (+/−) and homozygous (−/−) mutant mice. (A) Cytotoxic activities against alloantigens. Effector cells (H-2$^{b/d}$) were stimulated in vitro with irradiated allogeneic spleen cells from SWR (H-2$^1$) mouse strain as described in Experimental Procedures. Target cells were concanavalin A induced lymphoblasts from SWR and C57BL/6 (H-2$^b$) mice. (B) Anti-viral cytotoxic activities. Effector cells were from mice (H-2b) primed in vivo with vaccinia virus as described in Experimental Procedures. Target cells were YAC cells and MC57 cells either uninfected or infected with vaccinia virus.

$CD8^+$ T cells in mice have cytotoxic effector functions. To address the question whether peripheral T cells from mice without CD8 expression could mount a cytotoxic response against alloantigens, spleen cells of these mice ($H-2^{b/d}$) were stimulated with allogeneic cells ($H-2^q$). The cytotoxic activity of the responder cells after five days of stimulation was assessed in a standard $^{51}Cr$ release assay (FIG. 3A). T cells from heterozygous mice, which have a decreased level of CD8 expression, generated a cytotoxic response against $H-2^q$ alloantigens which was comparable to the response of T cells from wild-type mice. The homozygous mice lacking $CD8^+$ T cells, however, did not develop a significant cytolytic T cell response against the specific target cells.

Figure 3B:
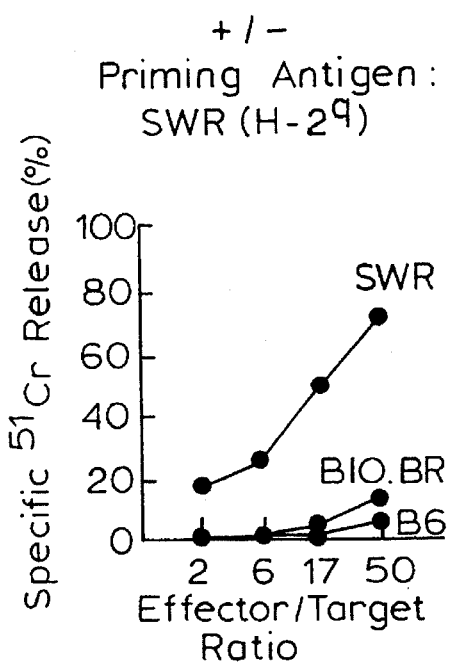
Figure 3C:
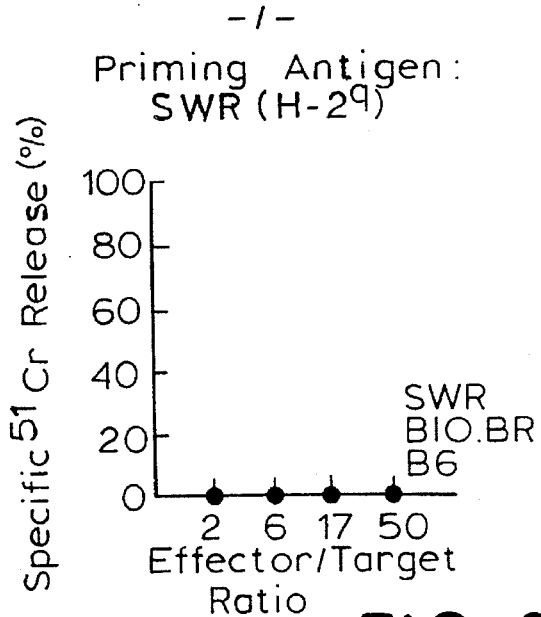
Figure 3D:
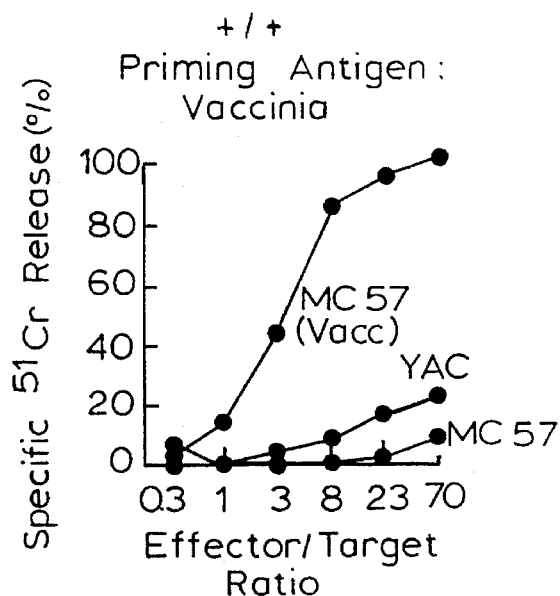
Figure 3E:
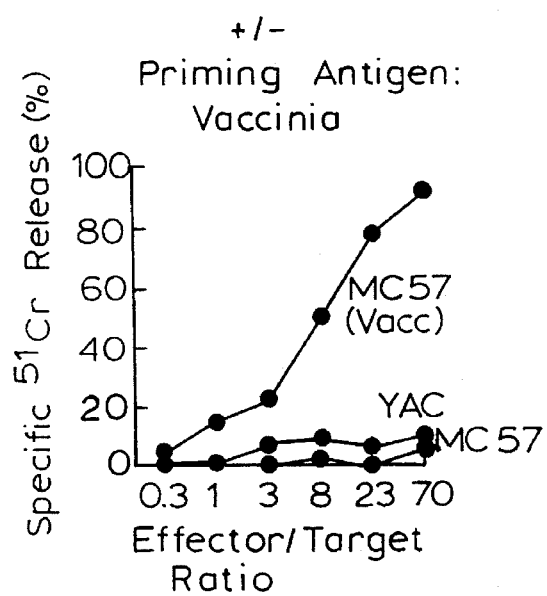
Figure 3F:
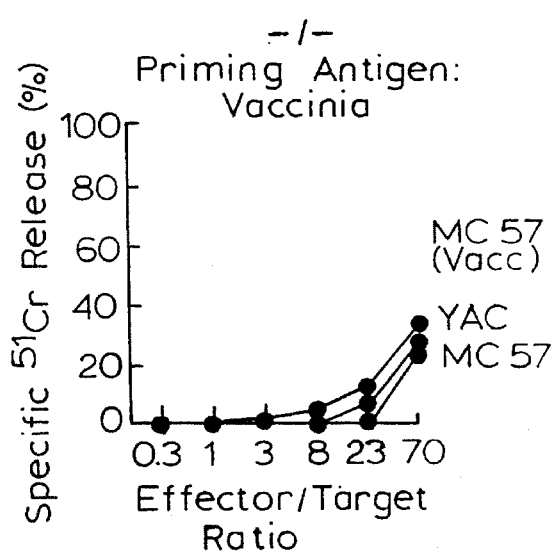

Mice infected with vaccinia virus mount a specific cytotoxic T cell response against the virus. The anti-viral cytotoxic function of T cells in mice primed in vivo with vaccinia infection was studied (FIG. 3B). Spleen cells from wild-type mice and mice heterozygous for the disrupted Lyt-2 gene lysed vaccinia infected MC57 cells but the lysis of uninfected MC57 cells or YAC cells was insignificant. The CD8 defective mice did not display a specific anti-vaccinia cytolytic activity although some nonspecific cytotoxicity was detected.

Although class I MHC restricted cytotoxic activity against alloantigens and viral antigens was not detected in bulk cultures, the possibility that very low numbers of cytotoxic T cells may be present in these mice has not yet been completely excluded.

Presence of $CD4^+$ Helper T Cells

Intrathymic maturation of helper T cells in mice defective in CD8 expression was studied by staining thymocytes with monoclonal antibodies specific for CD4 and other T Cell surface proteins. The sizes of thymocyte subsets identified by CD4 and CD8 (Lyt-2 and Lyt-3) surface expression appeared normal in Lyt-2 defective heterozygous mice despite lower levels of Lyt-2 and Lyt-3 expression (FIG. 2A and B). In homozygous mice, the $CD4^-CD8^-$ (double negative) population appears to be unchanged, but the population that would correspond to the $CD4^+CD8^+$ (double positive) stage seems to have merged with the $CD4^+CD8^-$ subpopulation.

Thymus and lymph node cells were examined by staining with monoclonal antibodies against CD4 and CD3 to study if the lack of surface expression of CD8 (Lyt-2 and Lyt-3) would affect the maturation of $CD4^+$ T lymphocytes. Thymocytes can be divided into three subpopulations ($CD3^-$, $CD3^{low}$ and $CD3^{high}$) with the level of CD3 expression corresponding to the degree of differentiation. Thymuses from homozygous mice contained immature T cells at the different stages of development and the ratio of the subpopulations was similar to that found in heterozygous and wild-type mice (FIG. 2C). These findings suggest that in the absence of surface Lyt-2 expression the process of thymic maturation and selection of $CD4^+$ T cells is relatively normal.

Figure 4:
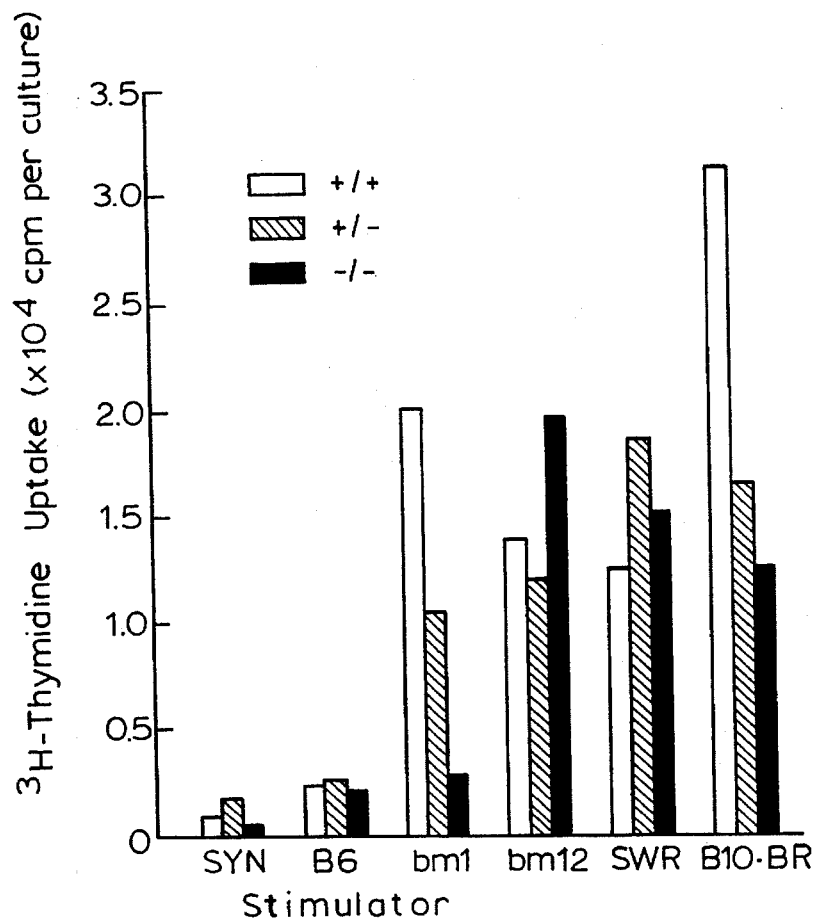
FIG. 4 shows proliferation of T cells from spleens of wild-type mice (+/+), heterozygous (+/−) and homozygous (−/−) mutant mice (H-2b) in response to allogeneic spleen cells from SWR (H-2$^q$), B10.BR (H-2$^k$), B6 bm12 (H-2$^{bm}$12), and B6 bm1 (H-2$^{bm1}$) mouse strains. Spleen cells from the same animal (SYN) and from C57BL/6 (H-2$^b$) mice were used as controls.

The proliferative potential of T cells from CD8 defective mice against alloantigens was studied. Spleen cells from these mice ($H-2^b$) were stimulated with allogeneic cells disparate in class I MHC ($H-2^{bm1}$), class II MHC ($H-2^{bm}12$) or both ($H-2^q$ and $H-2^k$). The responses in proliferation against complete H-2 differences and a class II MHC difference seemed to be similar among the three types of mice (FIG. 4) and interleukin-2 (IL-2) secretion was detected in these responses (data not shown). However, homozygous mice showed a decreased response against a class I MHC difference while the response of heterozygous mice was comparable to the response of wild-type mice. These data suggest that, although the $CD8^+$ T cells which recognize allogeneic class I MHC molecules were not detected in homozygous mice, $CD4^+$ T cells are functional and can respond to class II MHC alloantigens.

The in vivo anti-viral humoral response in mice defective in CD8 expression was studied by injecting mice with vesicular stomatitis virus (VSV). The efficiency of the humoral response was assessed by measuring levels of immunoglobulin M (IgM) and immunoglobulin G (IgG) virus neutralizing antibodies (Table 1). An early onset of anti-VSV IgM was detected on day 4 after viral infection. This was replaced by anti-VSV IgG by day 8 and the levels of IgG were still maintained on day 16 after infection. The levels of anti-VSV neutralizing IgM and IgG antibodies and their kinetics of induction were comparable among the wild-type mice and mice with the disrupted Lyt-2 genes. Since the switch from IgM to IgG is strictly dependent on helper T cells (Gupta et al., 1986), these results confirm that CD4+ helper T cells do provide help to B cells in mice defective in CD8 expression.

The present invention has enabled a showing that the absence of CD8 expression in the mutant mice prevents the development of class I MHC restricted cytotoxic T cells. Recognition of the appropriate class I MHC molecule by T cell receptor has been shown to be a decisive interaction for positive selection of cytotoxic T cells (Kisielow et al., 1988; Sha et al., 1988; Pircher et al., 1989). The data derived pursuant to the invention shows that the presence of CD8 is also necessary for the development of functional class I MHC restricted T cells. While the T cell receptor appears to recognize the polymorphic domains of the class I MHC molecule, CD8 most likely interacts with the monomorphic alpha-3 domain of class I MHC (Connolly et al., 1988; Salter et al., 1990). The lack of either one of these interactions results in the block of the development of cytotoxic T cells. The cytoplasmic portion of CD8 has been shown to be associated with a protein tyrosine kinase $P56^{lck}$ (Veillette et al., 1988; Barber et al., 1989; Rudd et al., 1989; Shaw et al, 1990; Turner et al., 1990) and could thus be involved in signal transduction during T cell ontogeny (Nakayama et al., 1989; Veillette et al., 1989). The importance of the cytoplasmic tail of CD8 could be studied by using the mice of the invention as recipients of transgenes carrying specific mutations of the CD8 gene.

In contrast to the lack of mature cytotoxic T cells, the maturation of class II MHC restricted helper T cells appears to be unaffected by the absence of CD8 surface expression. Hence, surface expression of CD8 on the early $CD8^+CD4^-$ $TcR^-$ population, as well as on the more mature $CD4^+CD8^+$ $TcR^{low}$ thymocyte population, is not obligatory for the differentiation of $CD4^+$ T lymphocytes. The proliferative response against class II MHC alloantigens and the helper T cell dependent B cell response following infection with VSV are normal in homozygous mice. These results indicate that $CD4^+$ T cells are functional in the mutant mice.

The mutant mouse strain provides a model of an immune system that specifically lacks the $CD8^+$ T cell population. Therefore, these mice should be valuable to study the involvement of $CD8^+$ T cells in infections, in the pathogenesis of autoimmune diseases and in the rejection of tumor or tissue transplants.

TABLE 1

Neutralizing anti-VSV response in mice defective in CD8 expression

| mouse strain (CD8 genotype) | Titers of neutralizing activities[a] ($\log_2 \times 10^{-1}$) in sera from mice after i.v. infection with VSV ($2 \times 10^6$ PFU) | | | | | | |
|---|---|---|---|---|---|---|---|
| | day 4 | | day 8 | | day 12 | | day 16 |
| | IgM | IgG | IgM | IgG | IgM | IgG | IgG |
| +/+ | 9 | <1 | 1 | 8 | 2 | 10 | 11 |
| | 10 | <1 | 1 | 8 | <1 | 11 | 10 |
| | 10 | <1 | <1 | 8 | <1 | 10 | 10 |
| | 10 | <1 | <1 | 8 | —[b] | — | — |
| +/− | 10 | <1 | 1 | 8 | <1 | 11 | 10 |
| | 9 | <1 | 2 | 8 | <1 | 10 | 10 |
| | 9 | <1 | 1 | 11 | <1 | 12 | 12 |
| | 10 | <1 | — | — | — | — | — |

TABLE 1-continued

Neutralizing anti-VSV response in mice defective in CD8 expression

| mouse strain (CD8 genotype) | Titers of neutralizing activities[a] ($\log_2 \times 10^{-1}$) in sera from mice after i.v. infection with VSV ($2 \times 10^6$ PFU) | | | | | | |
|---|---|---|---|---|---|---|---|
| | day 4 | | day 8 | | day 12 | | day 16 |
| | IgM | IgG | IgM | IgG | IgM | IgG | IgG |
| −/− | 8 | <1 | 1 | 7 | 1 | 9 | 8 |
| | 9 | <1 | 2 | 6 | 1 | 9 | 8 |
| | 9 | <1 | <1 | 9 | <1 | 12 | 11 |
| | 9 | <1 | 1 | 8 | <1 | 12 | 12 |

[a] Neutralizing IgM and IgG titers were determined as described in Experimental Procedures. Titers represent two-fold dilution steps of sera starting with 1:40.
[b] Not determined because mice had died.

EXPERIMENTAL PROCEDURES

Production of Mutant Mice Lacking CD8 Expression

The 2.2 kb HindIII-BamHI DNA fragment containing exon 1 to exon 3 of the Lyt-2 gene was used as a construct for homologous recombination. The 1.2 kb blunt-ended XhoI-BamHI fragment of the plasmid pMC1polA, which contains the neomycin resistant gene (Thomas and Capecchi, 1987), was inserted in opposite transcriptional orientation into the blunt-ended EcoRI site in the first exon of the Lyt-2 gene construct.

D3 embryonic stem cells from 129/J mice were maintained in the undifferentiated state either by growth on a feeder layer of mitomycin-C treated primary embryonic fibroblasts (Doetschman et al., 1985) or in culture medium supplemented with leukemia inhibitory factor (Smith et al., 1988).

Electroporation of embryonic stem cells, selection of G418-resistant colonies and polymerase chain reaction (PCR) screening for homologous recombination were carried out as described (Joyner et al., 1989). A primer specific for the neomycin resistance gene in the construct (5'-AACGCACGGGTGTTGGGTCGTTTG-3') (SEQ. ID NO. 1), and another primer specific for the Lyt-2 gene upstream of the construct (5'-ATTCAAGGCCAACCTTTGCC-3') (SEQ. ID NO. 2) were used in PCR. Homologous recombination was subsequently confirmed by genomic Southern blot hybridization. Chimeric mice were produced by injection of the embryonic stem cells into 3.5 day old blastocysts as described (Bradley, 1987). The contribution of embryonic stem cells to the germ-line of chimeric mice was assessed by breeding with (C57BL/6×DBA/2)F1 females and screening for agouti offspring. Germ-line transmission of the Lyt-2 mutation was confirmed by Southern analysis of the tail DNA and mice heterozygous for the mutant gene were interbred to homozygosity.

Flow Cytometric Analysis

Single cell suspensions from thymus and lymph nodes of 6–8 week old mice were made and $5\times10^5$ cells were stained with monoclonal antibodies for 30 minutes at 4° C. in 100 μl phosphate buffer saline containing 1% BSA and 0.1% sodium azide. Cells were then washed and analysed for single and double-colour flow cytometric analysis on a FACScan (Becton Dickinson, Inc.). Monoclonal antibodies used were: Lyt-2 (53-6.7, Becton Dickinson, Inc.), Lyt-3 (53-5.8, PharMingen, Inc.), L3T4 (GK1.5, Becton Dickinson Inc.), CD3 (145-2C11, PharMingen, Inc.), thy-1.2 (30-H12, Becton Dickinson, Inc.), and goat anti-mouse immunoglobulin G (Southern Biotechnology Associates, Inc.).

Cytotoxicity Assay

Cytotoxic assays were performed as described (Schilham et al., 1986). Alloreactive cytotoxic T lymphocytes were generated in a 5 day mixed lymphocyte culture. Responder spleen cells ($2\times10^6$/ml) were from adult (6–8 weeks) mice with normal, functional Lyt-2 gene (+/+), and mice heterozygous (+/−) and homozygous (−/−) for the disrupted Lyt-2 gene. These mice were of haplotype H-$2^{b/d}$. Stimulators were irradiated spleen cells ($5\times10^6$/ml, 3000 rad) from SWR (H-$2^q$) and C57BL/6 (H-$2^b$) mice. Target cells were lymphoblasts induced by concanavalin A (2.5 μg/ml) for three days and labelled with $^{51}$chromium (Amersham).

Cytotoxic T cells specific for viral antigens were generated as follows: mice were primed in vivo by intravenous injection of vaccinia-WR ($2\times10^6$ plaque forming unit (PFU)/mouse) 6 days prior to preparation of spleen cells. Target cells were MC57 fibroblasts infected with vaccinia-WR (5 PFU/cell) at the time of $^{51}$Cr labelling. Uninfected MC57 cells and YAC cells were used as controls for nonspecific cytotoxic activity.

The $^{51}$chromium release assay was performed by incubating $1\times10^4$ labeled target cells with different numbers of responder cells in a 0.2 ml culture medium in round-bottom microtiter plates. Plates were spun at 400 g for 5 minutes and then incubated for 4 hours at 37° C. After incubation, aliquots of supernatant were collected for determination of radioactivity in a γ-counter (LKB, Inc.) Percent specific lysis was calculated from cpm as 100×(experimental-spontaneous)/(total-spontaneous), whereas spontaneous release was determined in the absence of responder cells and total release was determined in the presence of 1N acetic acid. Each responder/target cell ratio was tested in duplicate.

Proliferation Assay

Responder cells were spleen cells from adult (6–8 weeks) mice with functional Lyt-2 gene and mice heterozygous and homozygous for the disrupted Lyt-2 gene. These mice were of haplotype H-$2^b$. Stimulator cells were irradiated (3000 R) spleen cells from the same mouse as the responder cells (syngeneic), and from mouse strains C57BL/6 (H-$2^b$), SWR(H-$2^q$), C57BL/6 bm1 (H-$^{bm1}$) or C57BL/6 bm2 (H-$2^{bm12}$). $5\times10^5$ Responder cells were cultured with $5\times10^5$ stimulator cells in a 0.2 ml culture medium for 3 days and $^3$H-thymidine uptake by cells after 16 hours incubation was determined in triplicates. The data represent the mean of triplicate determinations.

Neutralizing Antibody Determinations

Vesicular Stomatitis virus (Indiana strain) was injected intravenously ($2\times10^6$ PFU/mouse) into 6–8 week old wild-type mice and mice heterozygous and homozygous for the disrupted Lyt-2 gene. Four mice were used per group. Blood samples were collected on day 4, 8, 12 and 16 after infection. A virus neutralization assay was performed as previously described (Roost et al., 1988). The neutralizing antibody titer was defined as the highest dilution of serum that reduced the number of plaques to half of the control. The titer of IgG was determined after reduction of IgM by pre-treatment of sera with 0.1M B-mercaptoethanol in saline for 1 hour at room temperature (Scott and Gershon, 1970) before the assay. Titers of sera without β-mercaptoethanol treatment were taken as the total titers of both IgG and IgM.

Deposits

ES cell line with the disrupted Lyt-2 gene as shown in FIG. 1 has been deposited in the American Type Culture Collection, Rockville, Md., and given ATCC Accession No. CRL 11116.

REFERENCES

Barber, E. K., Dasgupta, J. D., Schlossman, S. F., Trevillyan, J. M., and Rudd, C. E. (1989) The CD4 and CD8 antigens are coupled to a protein-tyrosine kinase (p56$^{lck}$) that phosphorylates the CD3 complex. Proc. Natl. Acad. Sci. U.S.A. 86: 3277–3281.

Blanc, D., Bron, C., Gabert, J., Letourneur, F., MacDonald, H. R., and Malissen, B. (1988) Gene transfer of the Ly-3 chain gene at the mouse CD8 molecular complex: co-transfer with ly-2 polypeptide gene results in detectable cell surface expression of the ly-3 antigenic determinants. Eur. J. Immunol. 18: 613–619.

Bradley, A. (1987) Production and analysis of chimaeric mice in teratocarcinomas and embryonic stem cells (Robertson, E. J., ed) 113–151, *IRL Press*, Oxford, Washington, D.C.

Connolly, J. M., Potter, T. A., Wormstall, E. -M., and Hanson, T. H. (1988) The Lyt-2 molecule recognizes residues in the class I α3 domain in allogeneic cytotoxic T cell responses. J. Exp. Med. 168, 325–341.

Doetschman, T. C., Eistelter, H., Katz, M., Schmidt, W., and Kemler, R. (1985) The in vitro development of blastocyst-derived embryonic stem cell lines: formation of visceral yolk sac, blood islands and myocardium. J. Embryol. Exp. Morph. 87: 27–45.

Gorman, S. D., Sun, Y. H., Zamoyska, R. and Parnes, J. R. (1988) Molecular linkage of the Ly-3 and Ly-2 genes. Requirement of Lyt-2 for Ly-3 surface expression. J. Immunol. 140: 3646–3653.

Gosslet, A., Doetschman, T., Korn, R., Serfling, E., and Kemler, R. (1986) Mutagenesis by means of blastocyst-derived embryonic stem cell lines. Proc. Natl. Acad. Sci. U.S.A. 83: 9065–9069.

Gupta, S. C., Hengartner, H., and Zinkernagel, R. M. (1986) Primary antibody responses to a well-defined and unique hapten are not enhanced by preimmunization with carrier: analysis in a viral model. Proc. Natl. Acad. Sci. U.S.A. 83: 2604–2608.

Joyner, A., Skarnes, W. C., and Rossant, J. (1989) Production of a mutation in mouse En-2 gene by homologous recombination in embryonic stem cells. Nature 338: 153–155.

Kisielow, P., Bluthmann, H., Staerz, U. D., Steinmetz, M., and von Boehmer, H. (1988) Tolerance in T cell receptor transgenic mice involves deletion of nonmature CD4+8+ thymocytes. Nature 333: 742–746.

Ledbetter, I. A., Seaman, W. E., Tsu, T. T., and Herzenberg, L. A. (1981) Lyt-2 and Lyt-3 antigens are on two different polypeptide subunits linked by disulfide bonds. Relationship of subunits to T cell cytolytic activity. J. Exp. Med. 153: 1503–1516.

Liaw, C. W., Zamoyska, R., and Parnes, J. R. (1986) Structure, sequence, and polymorphism of the Lyt-2 T cell differentiation antigen gene. J. Immunol. 137: 1037–1043.

Nakauchi, H., Shinkai, Y., and Okumura, K. (1987) Molecular cloning of Lyt-3, a membrane glycoprotein marking a subset of mouse T lymphocytes: molecular homology to immunoglobulin and T-cell receptor variable and joining regions. Proc. Natl. Acad. Sci. U.S.A. 84: 4210–4214.

Nakayama, T., Singer, A., Hsi, E. P., and Samelson, L. E. (1989) Intrathymic signalling in immature CD4+CD8+ thymocytes results in tyrosine phosphorylation of the T-cell receptor zeta chain. Nature 341: 651–654.

Pircher, H., Mak, T. W., Lang, R., Ballhausen, W., Ruedi, E., Hengartner, H., Zinkernagel, R. M., and Burki, K. (1989) T cell tolerance to Mls$^a$ encoded antigens in T cell receptor V beta 8.1 chain transgenic mice. EMBO J. 8: 719–727.

Robertson, E., Bradley, A., Kuehn, M., and Evans, M. (1986) Germ-line transmission of genes introduced into cultured pluripotential cells by retroviral vectors. Nature 323: 445–447.

Roost, H., Charan, S., Gobet, R., Reedi, E., Hengartner, H., Althage, A., and Zinkernagel, R. M. (1988) An acquired immune suppression in mice caused by infection and lymphocytic choriomeningitis virus. Eur. J. Immunol. 18: 511–518.

Rudd, C. E., Anderson, P., Morimoto, C., Streuli, M. and Schlossman, S. F. (1989) Molecular interactions, T-cell subsets and a role of the CD4/CD8: p56$^{lck}$ complex in human T-cell activation. Immunol. Rev. 111: 225–266.

Salter, R. D., Benjamin, R. J., Wesley, P. K., Buxton, S. E., Garrett, T. P., Clayberger, C., Krensky, A. M., Norment, A. M., Littman, D. R. and Parham, P. (1990) A binding site for the T-cell co-receptor CD8 on the alpha 3 domain of HLA-A2. Nature 345: 41–46.

Schmidt-Ullrich, R. and Eichmann, K. (1990) Transfection of the CD8α gene restores specific target cell lysis: factors that determine the function and the expression of CD8 in a cytotoxic T cell clone. Int. Immunol. 2: 247–256.

Scott, D. W., and Gershon, R. K. (1970) Determination of total and mercaptoethanol-resistant antibody in the same serum sample. Clin. Exp. Immunol. 6: 313–317.

Sha, W. C., Nelson, C. A., Newberry, R. D., Kranz, D. M., Russell, J. H., and Loh, D. Y. (1988) Positive and negative selection of an antigen receptor on T cells in transgenic mice. Nature 336: 73–76.

Shaw, A. S., Chalupny, J., Whitney, J. A., Hammond, C., Amrein, K. E., Kavathas, P., Sefton, B. M., and Rose, J. K. (1990) Short related sequences in the cytoplasmic domains of CD4 and CD8 mediate binding to the amino-terminal domain of the p56$^{lck}$ tyrosine protein kinase. Mol. Cell. Biol. 10: 1853–1862.

Smith, A. G., Heath, J. K., Donaldson, D. D., Wong, G. G., Moreau, J., Stahl, M., and Rogers, D. (1988) Inhibition of pluripotential embryonic stem cell differentiation by purified polypeptides. Nature 336: 688–690.

Smithies, O., Gregg, R. G., Boggs, S. S., Koralewski, M. A., and Kucherlapati, R. S. (1985) Insertion of DNA sequences into the human chromosomal β-globin locus by homologous recombination. Nature 317: 230–234.

Thomas, K. R., and Capecchi, M. R. (1987) Site-directed mutagenesis by gene targeting in mouse embryo-derived stem cells. Cell 51: 503–512.

Turner, J. M., Brodsky, M. H., Irving, B. A., Levin, S. D., Perlmutter, R. M., and Littman, D. R. (1990) Interaction of the unique N-terminal region of tyrosine kinase p56$^{lck}$ with cytoplasmic dominas of CD4 and CD8 is mediated by cysteine motifs. Cell 60: 755–765.

Veillette, A., Bookman, M. A., Horak, E. M., And Bolen, J. B. (1988) The CD4 and CD8 T cell surface antigens are associated with the internal membrane tyrosine-protein kinase p56$^{lck}$. Cell 55: 301–308.

Veillette, A., Zuniga-Pflucker, J. C., Bolen, J. B., and Kruisbeek, A. M. (1989) Engagement of CD4 and CD8 expressed on immature thymocytes induces activation of intracellular tyrosine phosphorylation pathways. J. Exp. Med. 170: 1671–1680.

Walker, I. D., Hogarth, P. M., Murray, B. J., Lovering, K. E., Classon, B. J., Chambers, G. W., and McKenzie, I. F. C. (1984a) Ly antigen associated with T cell recognition and effector function. Immunol. Rev. 82: 47–77.

Walker, I. D., Murray, B. J., Hogarth, P. M., Kelson, A., and McKenzie, I. F. C. (1984b) Comparison of thymic and peripheral T cell Lyt-2, 3 antigens. Eur. J. Immunol 14: 906–910.

Zamoyska, R., Vollmer, A. C., Sizer, K. C., Liaw, C. W., and Parnes, J. R. (1985) Two Lyt-2 polypeptides arise from a single gene by alternative splicing patterns of mRNA. Cell 43: 153–163.

---

I claim:

1. A mutant mouse comprising disrupted alleles of the Lyt-2 gene, the disruption being introduced into the mouse or an ancestor of the mouse at an embryonic stage, wherein the disruption prevents the expression of the CD8 surface marker on T-lymphocytes of the mouse and results in a substantial decrease in the cytotoxic T lymphocyte response, and wherein the mouse expresses normal levels of Class I MHC proteins.

2. A mouse as claimed in claim 1, wherein the Lyt-2 gene is disrupted by homologous recombination by inserting a marker sequence in an exon of the Lyt-2 gene thereby disrupting its coding sequence.

3. A mouse as claimed in claim 2 wherein homologous recombination is accomplished using a construct comprising a HindIII-BamHI DNA fragment containing exons 1, 2 and 3 of the Lyt-2 gene, wherein exon I is interrupted by insertion of a marker for neomycin (G418) resistance into an EcoRI site of exon I.

4. A mouse as claimed in claim 3, wherein the construct is inserted into D3 embryonic stem cells by electroporation, and neomycin resistant colonies are screened for the homologous recombination event by the polymerase chain reaction.

* * * * *

UNITED STATES PATENT AND TRADEMARK OFFICE
CERTIFICATE OF CORRECTION

PATENT NO. : 5,530,178
DATED : June 25, 1996
INVENTOR(S) : Tak W. Mak

It is certified that error appears in the above-identified patent and that said Letters Patent is hereby corrected as shown below:

column 2, line 13, please replace "$(H-2^1)$" with --$(H-2^q)$--;

column 2, line 24, please replace "$(H-2^{bm}12)$" with --$(H-2^{bm12})$--;

column 4, line 41, please replace "$(H-2^{bm}12)$" with --$(H-2^{bm12})$--;

column 7, line 49, please replace "$(H-^{bm\prime})$" with --$(H-2^{bm\prime})$--;

column 9, line 19, please replace "Rëedi" with --Rüedi--; and column 10, line 19, please replace "Perimutter" with --Perlmutter--.

Signed and Sealed this

Fourteenth Day of October, 1997

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,530,178
DATED : June 25, 1996
INVENTOR(S) : Tak W. Mak

It is certified that error appears in the above-identified patent and that said Letters Patent is hereby corrected as shown below:

Title page;
[57] ABSTRACT, line 4, the phrase "mammals, for example," should be deleted.

Signed and Sealed this

Tenth Day of February, 1998

Attest:

BRUCE LEHMAN

*Attesting Officer*     *Commissioner of Patents and Trademarks*